United States Patent
Brahm

(10) Patent No.: US 10,835,558 B2
(45) Date of Patent: Nov. 17, 2020

(54) MAMMALIAN BIRTH TISSUE COMPOSITION FOR TUMOR TREATMENT

(71) Applicant: Brahm Holdings, LLC, Germantown, TN (US)

(72) Inventor: Timothy R. Brahm, Germantown, TN (US)

(73) Assignee: Brahm Holdings, Inc., Germantown, TN (US)

(*) Notice: Subject to any disclaimer, the term of this patent is extended or adjusted under 35 U.S.C. 154(b) by 0 days.

(21) Appl. No.: 16/385,226

(22) Filed: Apr. 16, 2019

(65) Prior Publication Data

US 2019/0314422 A1    Oct. 17, 2019

Related U.S. Application Data

(60) Provisional application No. 62/658,152, filed on Apr. 16, 2018.

(51) Int. Cl.
| | | |
|---|---|---|
| *A61K 35/50* | (2015.01) | |
| *A61K 35/51* | (2015.01) | |
| *A61K 39/00* | (2006.01) | |
| *A61K 38/20* | (2006.01) | |
| *C12N 5/0735* | (2010.01) | |
| *A61K 35/545* | (2015.01) | |

(52) U.S. Cl.
CPC .............. *A61K 35/50* (2013.01); *A61K 35/51* (2013.01); *A61K 38/2093* (2013.01); *A61K 39/0011* (2013.01); *A61K 35/545* (2013.01); *C12N 5/0606* (2013.01)

(58) Field of Classification Search
None
See application file for complete search history.

(56) References Cited

U.S. PATENT DOCUMENTS

| | | | |
|---|---|---|---|
| 2007/0025973 A1* | 2/2007 | Fitzsimmons | A61K 35/545 424/93.7 |
| 2011/0280849 A1* | 11/2011 | Zhang | A61K 31/198 424/93.71 |
| 2013/0189189 A1* | 7/2013 | Chang | A61K 35/44 424/9.34 |
| 2018/0311285 A1* | 11/2018 | Brahm | A61K 35/50 |
| 2019/0255127 A1* | 8/2019 | Wagner | A61K 35/44 |

OTHER PUBLICATIONS

Kazimirsky G. et al. Mesenchymal Stem Cells Enhance the Oncolytic Effect of Newcastle Disease Virus . . . Stem Cell Research & Therapy 7:149, Oct. 10, 2016. (Year: 2016).*

* cited by examiner

*Primary Examiner* — Ralph J Gitomer
(74) *Attorney, Agent, or Firm* — Barnes & Thornburg LLP

(57) ABSTRACT

The present disclosure generally relates to constructs, formulations and methods for the treatment of various types of cancer. The constructs, formulations and methods as provided herein are particularly useful for the treatment of various tumorigenic cancers.

10 Claims, No Drawings

MAMMALIAN BIRTH TISSUE COMPOSITION FOR TUMOR TREATMENT

CROSS-REFERENCE TO RELATED APPLICATIONS

The present application claims priority to U.S. Ser. No. 62/658,152 filed Apr. 16, 2018, the contents of which are incorporated in their entirety.

BACKGROUND OF THE INVENTION

Cancer results from an abnormal cell growth. The cells give up normal control mechanisms and thus are able to expand continuously, invade adjacent tissues, migrate to distant parts of the body, and promote the growth of new blood vessels from which the cells derive nutrients. Malignant cells may develop from any tissue within the body. As cancerous cells grow and multiply, they form a mass of cancerous tissue—called a tumor—that invades and destroys normal adjacent tissues. Tumors can be cancerous or noncancerous. A tumor may be visible on the skin or protrude outward from the body. Still other tumors are not evident until their presence begins to cause such symptoms as weight loss, fatigue, or pain. In some instances, tumors are located during routine tests. Cancerous cells from the primary site can metastasize throughout the body.

Benign tumors are typically asymptomatic but may cause specific symptoms depending on their anatomic location and tissue type. Benign tumors may grow outwards, producing large rounded masses, which can cause what is known as a "mass effect". Such growth can cause compression of local tissues or organs, which can cause many effects such as blockage of ducts, reduced blood flow, tissue death, and nerve pain or damage. Benign tumors may also produce hormones that can lead to life-threatening situations.

For treatment, higher grade tumors (grade III and IV), malignant tumors are more difficult to remove and require additional treatments beyond surgery, such as radiation or chemotherapy. Benign tumor removal also presents challenges and results in surgical stress on the body. Alternative forms of treatment of both malignant and benign tumors are still in need that do not have hazardous side effects.

SUMMARY OF THE INVENTION

According to one aspect, a method of arresting growth of or reducing the size of a tumor in a patient in need of such treatment is provided. The method includes the step of administering an effective amount of a mammalian birth tissue composition. According to one embodiment, the step of administration includes introducing the mammalian birth tissue composition intravenously. According to one embodiment, the step of administration includes introducing the mammalian birth tissue composition at or adjacent to a tumor site. According to one embodiment, the mammalian birth tissue composition is formulated as a membrane-based construct. According to one embodiment, the membrane-based construct includes at least one amnion membrane layer, chorion membrane layer, a full/intact amniotic membrane, or a combination thereof. According to one embodiment, the membrane-based construct includes two or more amnion membrane layers, chorion membrane layers, two or more full/intact amniotic membrane, or a combination thereof. According to one embodiment, the mammalian birth tissue composition is formulated as a flowable composition. According to one embodiment, the method further includes the step of forming an incision on or around a tumor prior to administering an effective amount of the mammalian birth tissue composition such that the mammalian birth tissue composition is introduced directly or adjacent to the tumor. According to one embodiment, the tumor is malignant. According to one embodiment, the tumor is benign.

DETAILED DESCRIPTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used in the specification, and in the appended claims, the words "optional" or "optionally" mean that the subsequently described event or circumstance can or cannot occur.

As used herein, the terms "bioabsorbable", "bioresorbable" and "biodegradable" may be used interchangeably and each refer to a material that dissolves in the body without causing a substantial immunological rejection or response.

As used herein, the term "mammalian birth tissue" includes, but is not limited to, elements of the placental organ such as, for example, the placental globe, the umbilical cord, the umbilical cord blood, the chorion membrane layer, the amnion membrane layer, the amniotic fluid, the full amniotic membrane, and other placental gelatins, fluids, cells and extracellular material obtained from a seronegative, healthy mammal.

As used herein, the term "mammalian birth tissue composition" refers to a membrane-based construct or a flowable composition.

As used herein, the term "placental tissue components" include amnion membrane layer, chorion membrane layer, Wharton's jelly, umbilical cord tissue, placental globe, other gelatins, other cells and extracellular matrix from mammalian birth tissue.

As used herein, the term "membrane" refers to an amnion membrane layer, a chorion membrane layer, a chorionic and an amnion membrane layer, or a full/intact amniotic membrane.

As used herein, the term "patient" refers to any and all mammals including, in particular, domesticated animals such as cows, horses, dogs, cats and sheep as well as primates including humans.

As used herein, the term "flowable" refers to a liquid-based formulation that is capable of being injected.

The present disclosure generally relates to constructs, formulations and methods for the treatment of various types of cancer. The constructs, formulations and methods as provided herein are particularly useful for the treatment of various tumorigenic cancers including, but not limited to, epithelial cancers, (e.g., pancreatic cancer, ovarian cancer, prostate cancer, lung cancer, breast cancer, colorectal cancer, and bladder cancer), and melanoma. According to one embodiment, the constructs, formulations and methods as provided herein arrest the growth of at least one tumor. According to one embodiment, the constructs, formulations and methods as provided herein cause tumor regression.

According to one embodiment, the constructs, formulations and methods as provided herein induce cancer cell death.

The constructs, formulations and methods as provided herein utilize mammalian birth tissue. To obtain such material, potential mammalian birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed). Mammalian birth tissue is preferably recovered from a full-term aseptic Cesarean delivery of a newborn. Alternatively, mammalian birth tissue is recovered from a full-term vaginal delivery of a newborn. The placental organ, including the placental globe, umbilical cord, associated membranes (chorion membrane layer and amnion membrane layer), other gelatins, fluids, cells and extracellular matrix can be recovered from a seronegative, healthy mammal after the newborn is removed. The placental globe, umbilical cord, other gelatins, fluids, cells and extracellular matrix can be removed and discarded or preserved for later use.

The membranes utilized in the constructs, formulations and methods as described herein may be produced by processing mammalian birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

The collected mammalian birth tissue is removed from any sterile shipment container and transferred aseptically to a sterile processing basin within the controlled environment. Once recovered, one or more of the placental tissue components can be removed via a sterile saline solution rinse, blunt dissection, scalpel, or a combination thereof, if necessary. According to one embodiment, the placental globe, umbilical cord, chorionic membrane, and other gelatins, fluids, cells and extracellular matrix are removed and discarded, leaving the amniotic membrane (amnion and chorion) for further processing. According to one embodiment, the mammalian birth tissue material is subject to the method of preparation described herein no more than four hours after recovery to preserve cell viability. According to one embodiment, the amnion and chorion are next carefully separated. According to one embodiment, amniotic fluid is retained upon recovery. The placental tissue components can them be placed in a sterile dish containing Plasma Lyte-A until further processing. According to one embodiment, Plasma Lyte-A is a sterile, nonpyrogenic isotonic solution where each 100 mL of solution contains 526 mg of sodium chloride, USP (NaCl); 502 mg of sodium gluconate ($C_6H_{11}NaO_7$); 368 mg of sodium acetate trihydrate, USP ($C_2H_3NaO_2 \cdot 3H_2O$); 37 mg of potassium chloride, USP (KCl); and 30 mg of magnesium chloride, USP ($MgCl_2 \cdot 6H_2O$). According to a preferred embodiment, the pH of the Plasma Lyte-A is between typically about 6.5 to typically about 8.0.

The membrane tissue (amnion and/or chorion) may then be subject to cross-linking and dehydration procedures. According to a preferred embodiment, a cross-linking agent that is nontoxic and non-immunogenic is utilized to treat the membrane tissue. According to one embodiment, the cross-linking agent generally possesses two or more functional groups capable of reacting with proteins to produce covalent bonds. According to one embodiment, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehydes such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy]succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and kethyl-3-[3-dimethylaminopropyl]carbodiimide hydrochloride, a bifunctional oxirane (OXR), or ethylene glycol diglycidyl ether (EGDE). According to one embodiment, the membrane tissue is treated with at least one cross-linking agent for at least one second. According to one embodiment, the membrane tissue is treated with at least one cross-linking agent for at least one minute. According to one embodiment, the membrane tissue is treated with at least one cross-linking agent for at least 5 minutes. According to one embodiment, the membrane tissue is treated with at least one cross-linking agent for at least 15 minutes. According to one embodiment, the membrane tissue is treated with at least one cross-linking agent for at least 60 minutes. According to one embodiment, the membrane tissue is treated with at least one cross-linking agent at a concentration of at least about 0.01%. According to one embodiment, the membrane tissue is treated with at least one cross-linking agent at a concentration of at least about 0.1%. According to one embodiment, the membrane tissue is treated with at least one cross-linking agent at a concentration of at least about 1%.

After the membrane tissue has been treated with the at least one cross-linking agent as provided herein, the membrane tissue may be dehydrated according to one embodiment. According to one embodiment, a chemical dehydration step is performed by contacting the membrane (e.g., amnion and/or chorion) with a polar organic solvent for a sufficient time and at a sufficient concentration to substantially or completely remove residual water present in the membrane tissue. The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. According to one embodiment, the membrane tissue is contacted with a polar organic solvent at room temperature for at least one minute. According to one embodiment, the membrane tissue is contacted with a polar organic solvent at room temperature for at least ten minutes. According to one embodiment, the membrane tissue is contacted with a polar organic solvent at room temperature for up to about two weeks.

According to one embodiment, the membrane tissue or other placental tissue components can then be cryopreserved according to methods commonly used in the art. The components can be soaked in cryoprotectant prior to cryopreservation. In one embodiment, the cryoprotectant is one commonly used in the industry, such as, for example, dimethyl sulfoxide (DMSO). In a preferred embodiment, the cryoprotectant is an amnion control rate freeze solution comprising typically about 44% volume of Plasma Lyte-A, typically about 36% volume of human albumin 25% solution, and typically about 20% volume of dimethyl sulfoxide. In another embodiment, the cryoprotectant is a commercially available cryoprotectant such as Synth-a-Freeze® available from Invitrogen. Any cryoprotectant specific to the birth tissue material described herein may be used. In one embodiment, cryopreservation is achieved using a controlled rate freezer, resulting in a 1° C. rate from nucleation to −35° C. and a 10° C. per minute cooling rate to a −90° C. end temperature. Any cryopreservation method commonly known in the art may be used.

According to one embodiment, after cryopreservation, the placental tissue components may be ground, pulverized, or morselized into pieces, morsels or particles. According to one embodiment, the pieces, morsels or particles may be formulated into a flowable formulation. According to one embodiment, the flowable formulation is injectable. According to a particular embodiment, the flowable, injectable mammalian birth tissue composition includes morselized amnion membrane layer, morselized chorion membrane layer, Wharton's jelly, morselized umbilical cord tissue, morselized placental globe, amniotic fluid, other gelatins, other cells and extracellular matrix from mammalian birth tissue.

Tissue morselization may occur by any art-recognized method of tissue disruption, including, but not limited to: milling, blending, sonicating, homogenizing, micronizing, pulverizing, macerating, or a combination thereof. In one embodiment, the placental tissue components are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, and an intermediate cooling time of no more than about five minutes. In another embodiment, a Freezer/Mille available from SPEX SamplePrep, LLC may be used.

According to one embodiment, a membrane-based construct is provided. According to one embodiment, the membrane-based construct may include one or more layers of at least one placental tissue component. According to a preferred embodiment, the membrane-based construct may include one or more layers of amnion, chorion, or a combination thereof prepared as provided herein.

Methods of treating cancer in a patient in need of such treatment are provided. According to one embodiment, methods of treating various tumorigenic cancers are provided. According to one embodiment, methods of arresting the growth of at least one tumor are provided. According to one embodiment, methods of tumor regression by suppressing the growth of tumor cells are provided. According to one embodiment, methods of inducing cancer cell death are also provided.

The methods as provided herein can be used to treat tumorigenic cancer cells and at least one tumor by having a significant effect on general cell death (e.g. by apoptosis). According to one embodiment, the methods provided herein can be used to treat tumorigenic cancer cells and at least one tumor by having a significant effect on cancerous cells (i.e., having a significant effect on cell death beyond mere arrest of growth). The mammalian birth tissue compositions as described herein may be administered less frequently compared to small molecule or radiation therapy to minimize or eliminate potential toxic side effects against normal, untransformed cells. The methods as provided herein are particularly useful when surgical removal of a tumor or cancer cells is determined to be an unacceptable form of treatment. The methods as provided herein may also be utilized in palliative surgery. According to such an embodiment, the mammalian birth tissue compositions as provided herein may be used to aid in the reduction or elimination of pain or bleeding at or around a tumor. By implementing the methods provided herein, the risk of spreading cancerous cells during the process of removing abnormal or cancerous tissue (i.e., seeding) is eliminated.

Prior to administration, the presence of tumor cells in an individual may be determined by performing a biopsy on tissue suspected to be cancerous, or determined from body fluid samples (e.g., from cells purified or isolated from a blood sample). Biopsy may be performed by aspiration, needle, incisional, or excisional. Cancerous cells or tissues can then be characterized using a variety of biological, molecular, morphological, and cytological means. Biological and molecular markers can be used to assess characteristics such as the type of cell origin (such as an epithelial cell), specific type of cell (such as organ type like breast or prostate), cell growth or cell growth potential, cell growth arrest, and hyperploidy status. Cellular markers include, but not limited to, molecular, biochemical, and biological markers and probes that are used alone or in combination. Once located, the methods as provided herein may be performed.

According to each method provided herein, either a flowable formulation of mammalian birth tissue or a membrane-based construct may be administered by a user (i.e., medical professional) by direct application over or adjacent to the chosen site of cancer cells or tumors. Any administration may be a single application or multiple applications. Administrations may be to a single site or to more than one site in the individual to be treated. Multiple administrations may occur essentially at the same time or separated in time. According to one embodiment, the tumor may arise from astrocytes in the cerebral hemispheres of the brain or spinal cord. According to a particular embodiment, the tumor may be a glioblastoma.

According to a particular embodiment, a flowable composition may be administered by a user (i.e., medical professional) either through direct injection or by direct application over or adjacent to the chosen site. Modes of administration may include, but are not limited to: intramuscular, subcutaneous, intraperitoneal, percutaneous, soft tissue injection, surgical placement, arthroscopic placement, intravenous, intravascular, intracerebral, transdermal, topical or mucosal. According to one embodiment, the flowable formulation is administered at the site or sites of cancer cells or tumors. According to one embodiment, tumor growth is arrested upon administration. According to one embodiment, tumor growth is regressed upon administration. According to one embodiment, cancer cell death is induced upon administration.

According to another particular embodiment, a membrane-based construct may be administered by a user (i.e., medical professional) by direct application over or adjacent to a site where cancers cells are believed to be or where a tumor may have been located. According to one embodiment, an incision is made adjacent at the site of the tumor and at least one membrane-based construct is placed inside a space made by the incision. The incision is then closed with the membrane-based construct in place. Care is taken to not cause disruption of the tumor so as to result in seeding. According to one embodiment, an incision is made substantially above the tumor. Upon opening the incision, at least one membrane-based construct is placed in substantial contact with the tumor. Care is taken to not cause disruption of the tumor so as to result in seeding.

According to another embodiment, the mammalian birth tissue compositions as described herein may be administered alone or in conjunction with a virus. According to another embodiment, the mammalian birth tissue compositions as described herein may be administered alone or in conjunction with a virus to preferentially target and kill cancer cells. According to another embodiment, the mammalian birth tissue compositions as described herein may be administered alone or in conjunction with a virus to preferentially target and kill human glioblastoma stem cells. According to another embodiment, the mammalian birth tissue compositions as described herein may be mixed with a virus and administered to a mammalian brain to suppress or kill cancer cells or human glioblastoma stem cells. The mammalian birth tissue compositions as described herein may function as a delivery vector for delivery of the a virus to a mammalian brain to suppress or kill cancer cells. According to one embodiment, the mammalian birth tissue compositions and virus as described herein may be administered directly to a mammalian brain during brain surgery. According to one embodiment, the mammalian birth tissue compositions and virus as described herein may be administered directly into the blood stream via an artery in a patient's groin. According to one embodiment, the mammalian birth tissue compositions and virus as described herein may be administered directly to a site in the upper body such as the heart or brain via an angioplasty-type procedure performed via routing through an artery in the groin. According to one embodiment, the virus is Zika, measles, polio, herpes or a combination thereof.

According to another embodiment, the mammalian birth tissue compositions as described herein may be administered alone or in conjunction with at least one flowable biologic component. The at least one flowable biologic component is any therapeutic agent that suppresses a tumor or causes tumor regression. According to one embodiment, the at least one flowable biologic component is selected from the group consisting of DNA, RNA, chemotherapeutic agents, Minimum Essential Medium, Dulbecco's Modified Eagle's Medium, Plasma Lyte-A, human albumin 25% solution, calcium-rich water, alkaline ionized water, acidic ionized water, pharmaceutical grade water, neutral pH saline, donor blood, platelet rich plasma, or a combination thereof.

According to one embodiment, tumor growth is arrested upon administration according to the methods provided herein. According to one embodiment, tumor growth is regressed upon administration according to the methods provided herein. According to one embodiment, cancer cell death is induced upon administration according to the methods provided herein.

Examples of tumors which may be treated according to the methods provided herein include, but are not limited to, malignant tumors as a result of epithelial cancers, e.g., prostate cancer, lung cancer (e.g., lung adenocarcinoma), pancreatic cancers (e.g., pancreatic carcinoma such as, for example, exocrine pancreatic carcinoma), brain cancers, breast cancers, colon cancers (e.g., colorectal carcinomas, such as, for example, colon adenocarcinoma and colon adenoma), ovarian cancer, bladder carcinoma, and cancers of the liver. Other cancers that can be treated include melanoma, myeloid leukemias (for example, acute myelogenous leukemia), sarcomas, thyroid follicular cancer, and myelodysplastic syndrome.

Benign tumors may also be treated according to the methods as provided herein. Benign tumors are usually removed if problems such as seizure or discomfort are caused by the tumor. In such cases, benign tumors may be removed via surgical means. When surgical resection is required, the methods provided herein may be employed to reduce complications generally associated with surgical procedures.

A kit for use by a medical professional is also provided. According to one embodiment, the kit includes one or more packaged membrane-based constructs or at least one packaged flowable formulations as provided herein. The packaged flowable formulation may include a surgical syringe filled with an appropriate amount of flowable mammalian birth tissue composition. According to a particular embodiment, the kit includes individual construct layer materials that may be packaged individually and shipped together for assembly at the time of use. According to a particular embodiment, the kit includes in a single construct ready for administration upon opening the package. According to one embodiment, the kit may include one or more components to aid the surgical professional in assembly and/or implantation including sutures or tissue glue/adhesive. The kit may further include at least one set of instructions. The kit may further include a container adapted to accommodate and preserve the aforementioned components per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

I claim:

1. A method of arresting growth of or reducing the size of a tumor in a patient in need of such treatment, the treatment comprising
    administering an effective amount of a mammalian birth tissue composition to a patient in need,
    wherein the mammalian birth tissue composition comprises at least one virus and ground chorion.

2. The method of claim 1, wherein the step of administration comprises introducing the mammalian birth tissue composition intravenously.

3. The method of claim 1, wherein the step of administration comprises introducing the mammalian birth tissue composition at or adjacent to a tumor site.

4. The method of claim 1, wherein the mammalian birth tissue composition is formulated as a flowable composition.

5. The method of claim 1, further comprising the step of forming an incision on or around a tumor prior to administering an effective amount of the mammalian birth tissue composition such that the mammalian birth tissue composition is introduced directly or adjacent to the tumor.

6. The method of claim 1, wherein the tumor is malignant.

7. The method of claim 1, wherein the tumor is benign.

8. The method of claim 1, further comprising the step of mixing a virus with the ground chorion prior to administration.

9. The method of claim 8, wherein the virus is Zika, measles, polio, herpes or a combination thereof.

10. The method of claim 8, wherein the tumor comprises glioblastoma stem cells.

\* \* \* \* \*

UNITED STATES PATENT AND TRADEMARK OFFICE
CERTIFICATE OF CORRECTION

PATENT NO. : 10,835,558 B2  
APPLICATION NO. : 16/385226  
DATED : November 17, 2020  
INVENTOR(S) : Timothy R. Brahm Page 1 of 1

It is certified that error appears in the above-identified patent and that said Letters Patent is hereby corrected as shown below:

On the Title Page

Item (73) Assignee:
"Brahm Holdings, Inc." should be --Brahm Holdings, LLC--

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*